(12) United States Patent
Peltier

(10) Patent No.: US 8,969,031 B2
(45) Date of Patent: *Mar. 3, 2015

(54) AUTOMATED CELL DENSITY ADJUSTMENT METHOD FOR PRODUCING AN ANALYSIS PLATE

(75) Inventor: Eric Peltier, Clamart (FR)

(73) Assignee: Novacyt, Velizy Villacoublay (FR)

( * ) Notice: Subject to any disclaimer, the term of this patent is extended or adjusted under 35 U.S.C. 154(b) by 817 days.

This patent is subject to a terminal disclaimer.

(21) Appl. No.: 12/681,376

(22) PCT Filed: Oct. 7, 2008

(86) PCT No.: PCT/FR2008/051808
§ 371 (c)(1),
(2), (4) Date: Apr. 2, 2010

(87) PCT Pub. No.: WO2009/053602
PCT Pub. Date: Apr. 30, 2009

(65) Prior Publication Data
US 2010/0221772 A1    Sep. 2, 2010

(30) Foreign Application Priority Data
Oct. 9, 2007    (FR) ...................... 07 58160

(51) Int. Cl.
*C12P 1/00* (2006.01)
*G01N 1/28* (2006.01)

(52) U.S. Cl.
CPC ........ *G01N 1/2813* (2013.01); *G01N 2001/282* (2013.01); *G01N 2001/2826* (2013.01)
USPC .......................................................... 435/41

(58) Field of Classification Search
USPC .......................................................... 435/41
See application file for complete search history.

(56) References Cited

U.S. PATENT DOCUMENTS 6,627,158 B1    9/2003 Peltier

FOREIGN PATENT DOCUMENTS

| EP | 1 775 571 A2 | 4/2007 |
|----|---|---|
| FR | 2 792 333 A1 | 10/2000 |
| WO | 87/07024 A1 | 11/1987 |
| WO | 99/44743 A1 | 9/1999 |

OTHER PUBLICATIONS

Kim et al. "A hybrid bioreactor for high density cultivation of plant cell suspensions" Appl Microbiol Biotechnol., 1991, 34:726-729.*
Crane et al. "Host cell death due to enteropathogenic *Escherichia coli* has features of apoptosis", Infection and Immunity, 1999, 67(5):2575-2584.*
Lab-Tek chamber slide data sheet, 2011, pp. 1-4.*
Frachon et al. "Multiple microfermentor battery: a versatile tool for use with automated parallel cultures of microorganisms producing recombinant proteins and for optimization of cultivation protocols", Applied and Environmental Microbiology, 2006, 72(8):5225-5231.*
Adams et al. "Clinical significance of unsatisfactory conventional pap smears owing to inadequate sequamous cellularity defined by the Bethesda 2001 Criterion", Am J Clin Pathol., 2005, 123:738-743.*
International Search Report, dated May 12, 2009, from corresponding PCT application.

\* cited by examiner

*Primary Examiner* — Bin Shen
(74) *Attorney, Agent, or Firm* — Young & Thompson

(57) ABSTRACT

This method includes the following steps of:
  taking a sample of a cell solution from a sample flask,
  placing the sampled solution in a decantation chamber (2) arranged above the analysis plate (4),
  allowing the solution to decant in order to obtain a thin layer of cells on the analysis plate (4). It includes a step of measuring the cell density of the sampled solution, the measurement being carried out in the decantation chamber (2). A device for producing a cell analysis plate allowing such a method to be carried out is also described.

13 Claims, 2 Drawing Sheets

AUTOMATED CELL DENSITY ADJUSTMENT METHOD FOR PRODUCING AN ANALYSIS PLATE

CROSS REFERENCE TO RELATED APPLICATIONS

This Patent Application is a 371 National Stage entry of the Patent Cooperation Treaty Application No. PCT/FR2008/051808 filed on Oct. 7, 2008, entitled, "AUTOMATED CELL DENSITY ADJUSTMENT METHOD FOR PRODUCING AN ANALYSIS PLATE," the contents and teachings of which are hereby incorporated by reference in their entirety.

BACKGROUND OF THE INVENTION

1. Field of the Invention

The present invention relates to a method for producing a cell analysis plate of the type comprising a thin layer of cells or a cell dispersion to be analysed provided on an analysis plate, the method comprising the following steps of:
 taking a sample of a cell solution from a sample flask,
 placing the sampled solution in a decantation chamber which is arranged above the analysis plate,
 allowing the solution to decant in order to obtain the thin layer of cells on the analysis plate. The invention also relates to a device for producing a cell analysis plate allowing such a method to be carried out.

2. Description of the Related Art

Cell analysis plates are produced, for example, in order to establish medical diagnoses. To that end, a deposit of cells is carried out on a glass slide.

A sample of the cells is taken by means of a sample brush, for example, by means of a smear, then the brush is arranged in a sample flask where the cells are placed in solution. A sample of a portion of the cell solution is then taken and placed in a decantation chamber located above the glass slide. After decantation and absorption of the cell admixture liquid, a thin layer of cells or cell dispersion is obtained on the glass slide and forms the analysis plate. Such a method is described, for example, in document FR-2792333.

It is desirable to obtain a thin layer or dispersion having constant cell density and in particular to have enough cells present to obtain a relevant diagnosis. In some applications, such as smears for screening for cancer of the cervix of the uterus, the number of cells must comply with the Bethesda classification which is a classification for standardising the diagnosis result of the smears, and each dispersion must thus comprise more than 5000 cells. Therefore, an adjustment of the number of cells sampled may be necessary if the density of the cells is not sufficient in the solution.

Currently, the measurement of the cell density is carried out on the cells present in the sample flask. That is to say that the sample is taken then placed in the flask, where it is dissolved and the density measurement is carried out in order to establish what quantity of cell suspension it is necessary to add to the cells on the analysis plate in order to have enough of them when the diagnostic reading is carried out. The density measurement is, for example, carried out by nephelometric analysis, that is to say, by measuring the diffraction of light which passes through the flask.

However, this type of measurement in the flask has a number of disadvantages. Firstly, the measurement is very unreliable because the sample brush present in the flask or the administrative label for identifying the flask that is adhesively bonded thereto can disrupt the measurement. On the other hand, the measuring method involves all the cell elements present in the flask, such as the epithelial cells, red blood corpuscles, inflammatory cells, etc., without distinction and does not allow selective measurement of the cells which are representative of and relevant to the diagnosis of the sample. Finally, if the quantity of cell suspension is adjusted directly during the sampling in the flask in order to obtain at once an analysis plate having optimum cell density, there is no complete automation for the procedure which remains open, nor any follow-up quality operation allowing a report to be produced setting out the low cell density of the solution initially present in the sample flask and allowing it to be corrected on the analysis plate by secondary enrichment.

BRIEF SUMMARY OF THE INVENTION

An object of the invention is to overcome those disadvantages by providing a method for producing an analysis plate of the above-mentioned type, allowing measurement of cell density that is reliable, pertinent and allows a quality follow-up operation in the event of corrections.

To that end, the invention relates to a method for producing an analysis plate of the above-mentioned type, in which the method is characterised in that it comprises a step of measuring the cell density of the sampled solution, the measurement being carried out in the decantation chamber.

According to other features of the method:
 the production method comprises a step of comparing the cell density measured with a threshold density;
 the production method comprises a step of sampling an additional cell solution and adding that sampled solution to the decantation chamber if the cell density measured is less than the threshold density;
 the threshold density is substantially equal to 5000 cells per thin layer of cells;
 the cell density is measured by diffraction of light or by counting the cells on a given surface; and
 the step of measuring the cell density comprises a step of illuminating the decantation chamber.

The invention also relates to a device for producing a cell analysis plate of the type comprising at least one cell sample flask, a decantation chamber which is arranged on an analysis plate, means for sampling a cell solution from the sample flask and introducing the solution into the decantation chamber, characterised in that it further comprises means for measuring the cell density in the decantation chamber so as to produce an analysis plate as defined above.

This device further comprises means for measuring the cell density in the sample chamber so as to produce an analysis plate in accordance with a method as described above.

According to other features of the device:
 the means for measuring the cell density comprise means for illuminating the decantation chamber and means for measuring the diffraction of light or counting cells on a given surface;
 the means for measuring the diffraction of light or counting cells on a given surface comprise a camera; and
 the camera is carried by a movable arm, the arm moving above a plurality of decantation chambers which are arranged above a plurality of analysis plates.

BRIEF DESCRIPTION OF THE DRAWINGS

Other aspects and advantages of the invention will be appreciated from the following description which is given by way of example and with reference to the appended drawings, in which.

DETAILED DESCRIPTION OF THE PREFERRED EMBODIMENTS

Figure 1:
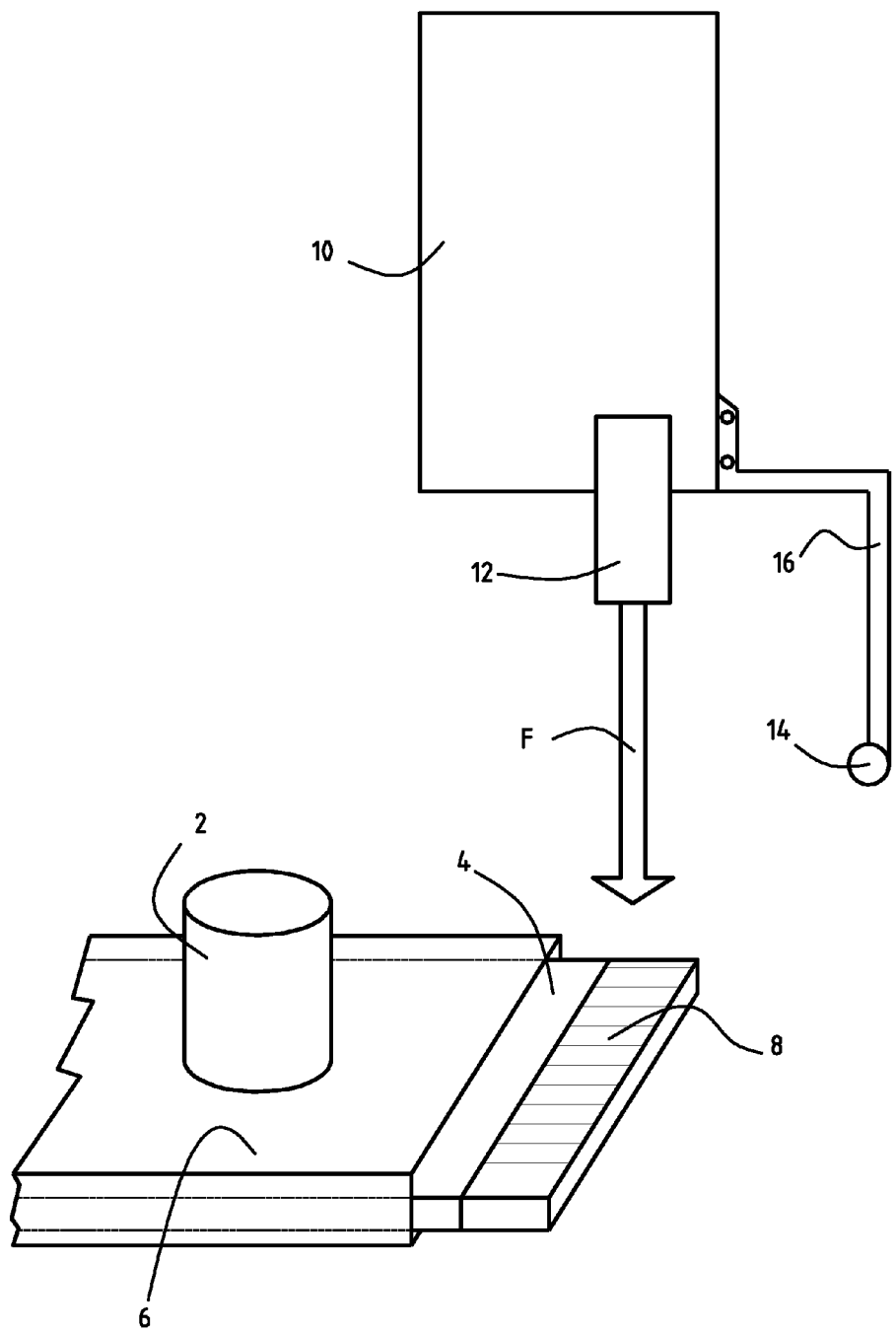
FIG. 1 is a schematic perspective part-illustration of a device for producing an analysis plate according to one embodiment of the invention.

For the purposes of simplification, the device for producing an analysis plate has not been illustrated in its entirety in the Figures.

This device generally comprises at least one cell sample flask (not illustrated), at least one decantation chamber 2 which is arranged on an analysis plate 4, means (not illustrated) for sampling a cell solution from the sample flask and for introducing the solution into the decantation chamber 2.

The sample flask and the decantation chamber 2 are arranged in a plate 6 which is provided with at least one housing for receiving an analysis plate 4 below the decantation chamber 2. In practice, a plurality of decantation chambers 2 and analysis plates 4 are provided in corresponding indentations of the plate 6 for constructions of analysis plates in series.

The decantation chamber 2 is a bottomless receptacle so that the contents introduced into the chamber are poured on the analysis plate, as is described, for example, in document FR-2792333. The analysis plate 4 is a conventional glass slide for this type of application.

The sampling and introduction means comprise, for example, an automated pipette (not illustrated) which is capable of moving from the sample flask to a decantation chamber 2 and which is actuated in order to take a sample of the contents from the flask and to introduce it into the chamber 2.

According to one embodiment, the pipette is further provided in order to take a sample of a liquid for diluting the cell solution sampled in the flask and to mix that liquid with the solution in the pipette in order to dilute the solution sampled and to introduce it into the decantation chamber 2 again.

A smear is taken and deposited in the sample flask. At that location, it is subjected to processing in order to select the relevant cells for analysis, as is known per se. The solution obtained is sampled by the sampling means and may be diluted then introduced into the decantation chamber 2 in an automated manner.

The solution is left to decant in the chamber 2 in order to obtain a layer of cells or cell dispersion on the analysis plate 4 by absorption of the liquid from the solution.

The analysis plate comprises, at an outermost portion, an identification means, for example, of the bar code type 8. According to other embodiments, the identification means are different, for example, a label carrying information or an electronic chip of the RFID chip type whose contents can be read remotely by reading means.

An arm 10 is movable above the plate 6. The arm carries a camera 12 which is provided to record images of the plate 6, that is to say, of the contents of the decantation chamber 2 and the analysis plate 4, as illustrated by the arrows F and F' of FIGS. 1 and 2, respectively.

During a first step illustrated in FIG. 1, the arm 10 is positioned in such a manner that the camera 12 is orientated towards the bar code 8 and reads the identification information of the analysis plate 4. That information is, for example, transmitted to a data-processing system which brings about the quality follow-up operation of a plurality of analysis plates and combines information concerning the thin layer of cells or cell dispersion provided on each plate.

According to the embodiment illustrated in the Figures, the camera 12 also forms means for measuring the cell density of the sampled solution present in the decantation chamber.

Figure 2:
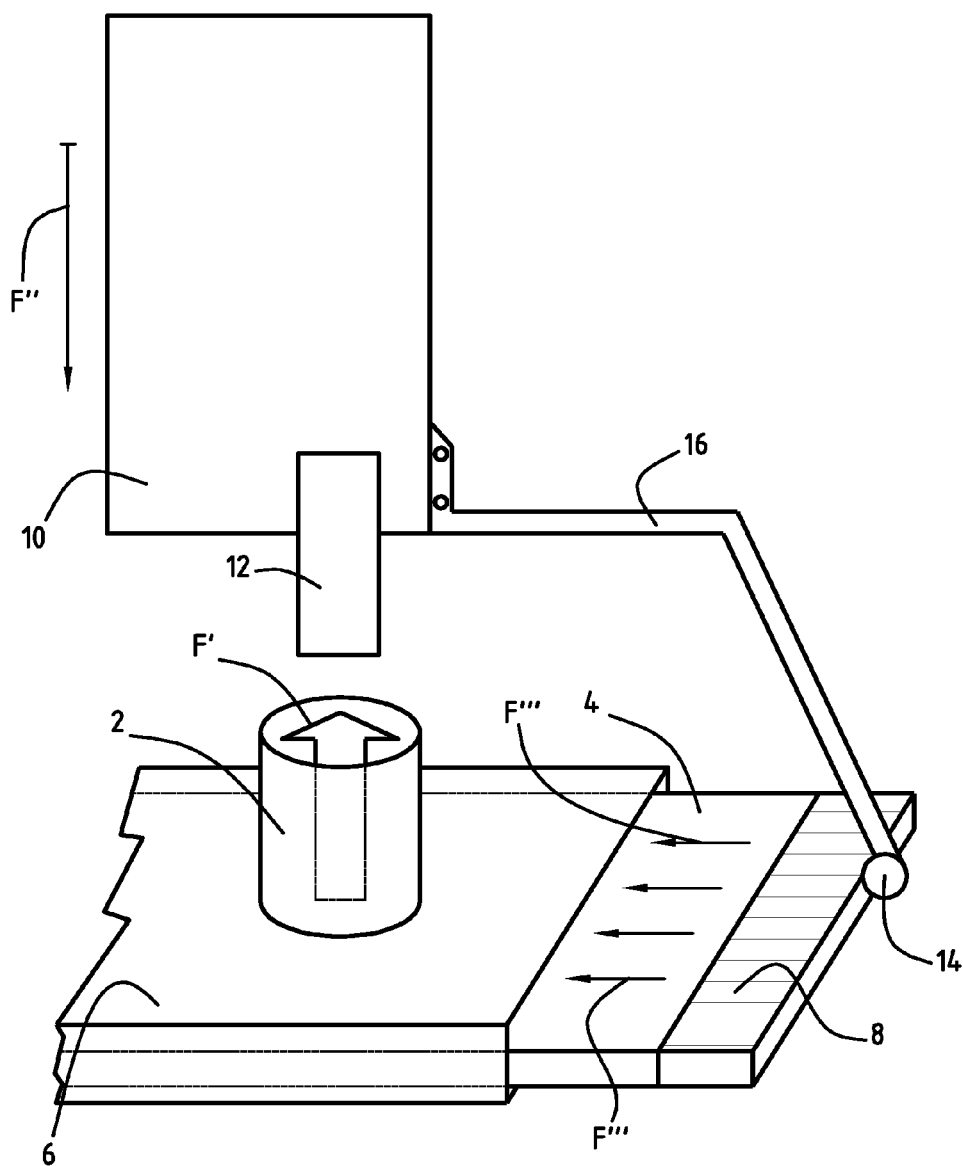
FIG. 2 is a schematic illustration of the device of FIG. 1 during a step of measuring the cell density of a solution present in a decantation chamber.

To that end, the arm 10 is lowered, as illustrated by the arrow F″ of FIG. 2 and is moved above the decantation chamber 2 in order to acquire the images of the contents of that chamber, as illustrated by the arrow F'. That movement may extend as far as contact with the decantation chamber in order to obtain sealing with respect to light, producing a dark room in order to optimise the quality of acquisition of the images.

The means for measuring the cell density further comprise means for illuminating the decantation chamber in order to allow the camera 12 to carry out the density measurement. According to the embodiment illustrated in the Figures, the arm 10 carries a light source 14 which is arranged at the outermost portion of an elastic and resilient metal plate 16. When the arm 10 is lowered, the light source 14 moves into contact with the edge of the analysis plate 4, then, when the arm 10 is moved above the decantation chamber 2, the plate 16 becomes deformed so as to fix the light source 14 in position, as illustrated in FIG. 2. The movement of the arm 10 allows the light source 14 to be positioned against the analysis plate 2 in order to have optimum transmission of light. The light source 14 diffuses light in the analysis plate, as illustrated by the arrows F''' of FIG. 2. The illumination of the decantation chamber 2 is therefore carried out laterally. The light source 14 is, for example, an electroluminescent diode (ELD). The illumination means are particularly advantageous because they are independent of the plate 6 and are easy to maintain. The means are further inexpensive to implement.

The camera 12 measures the cell density by measuring the diffraction of light by the cell solution in the decantation chamber or by counting cells on a given surface. Those measurement methods are known per se and will not be described in detail here. The camera 12 has a cell resolution which is sufficient for this type of measurement.

According to another embodiment which is not illustrated, a specific camera for measuring the density is provided in addition to the camera 12 for reading the identification means 8. The specific camera, which is also carried by the arm 10, is more effective than the camera 12, in particular in terms of resolution, and is specifically dedicated to measuring the cell density.

According to other embodiments which are not illustrated, the illumination of the decantation chamber 2 is carried out differently. In this manner, there are provided, for example, light guides, for example, of the fibre optic type, which are provided in the plate 6 so as to be in contact with the edges of the analysis plate(s) 4 in order to laterally illuminate the decantation chambers 2. Alternatively, a light source is positioned on the arm 10 so as to illuminate the decantation chamber 2 from above. The light source is positioned and arranged to avoid problems involving interference reflections at the surface of the sampled solution present in the decantation chamber 2. According to another alternative, the light source illuminates the decantation chamber 2 from below. The plate is adapted and has inspection holes which allow light to pass through.

The density measured by the means described above is compared with a threshold density which is substantially equal to the minimum density to be had in order to obtain a relevant analysis of the thin layer of cells or cell dispersion. That comparison is carried out, for example, by the data-processing system described above. According to one embodiment, the threshold density is substantially equal to 5000 cells per cell dispersion, as set out by the Bethesda classification.

If the density measured is less than the threshold density, the method for producing analysis plates comprises an additional step of adjusting the cell density of the dispersion. The sampling means take a sample of a volume of an additional cell solution from the sample flask and introduce it into the decantation chamber 2 in order to add cells to the thin layer of cells or cell dispersion after decantation. The additional volume to be sampled is, for example, calculated beforehand by the data-processing system and the automatic sampling means are controlled accordingly.

The information, according to which an adjustment of the density has been carried out, is recorded by the data-processing system in relation to the identity of the analysis plate 4 in order to allow a quality follow-up operation for the cell sample.

The method and the device described above allow a measurement of the density to be obtained that is reliable because it is carried out directly in the decantation chamber 2 and not in the sample flask. The measurement further involves only the cells relevant to the analysis. The measurement also allows a quality follow-up operation to be brought about, allowing production of a report setting out the low cell density of the solution present in the sample flask and correction thereof on the analysis plate by secondary enrichment.

The invention claimed is:

1. A method for producing a cell analysis plate with sufficient cell density for medical diagnosis, comprising a thin layer of cells to be analyzed provided on an analysis plate, the method comprising:
   taking a sample of a cell solution from a sample flask, said cells being from a subject for medical diagnosis;
   placing the sampled solution in a decantation chamber which is arranged above the analysis plate;
   measuring, directly in the decantation chamber, a cell density of the sampled cell solution;
   comparing the measured cell density with a threshold minimum cell density, and if the measured cell density is less than the threshold minimum cell density, then taking an additional sample of the cell solution from the sample flask and adding the additional sample solution to the decantation chamber; and
   decanting the cell solution from the decantation chamber and allowing the cells to form the thin layer of cells on the analysis plate.

2. The method according to claim 1, wherein the threshold minimum cell density is about 5000 cells per thin layer of cells.

3. The method according to claim 2, wherein the cell density is measured by diffraction of light or by counting cells of the thin layer of cells on a given surface.

4. The method according to claim 1, wherein the cell density is measured by diffraction of light or by counting cells of the thin layer of cells on a given surface.

5. The method according to claim 4, wherein measuring the cell density comprises illuminating the decantation chamber.

6. The method according to claim 1, wherein the analysis plate is a glass slide.

7. The method according to claim 1, further comprising diluting the sample of the cell solution taken from the sample flask before placing the sampled solution in the decantation chamber.

8. The method according to claim 1, wherein measuring the cell density comprises:
   illuminating the decantation chamber; and
   measuring diffraction of light by the cell solution in the decantation chamber.

9. The method according to claim 1, further comprising calculating an amount of the additional sample solution required to produce the cell density greater than or equal to the threshold minimum cell density, and adding said amount of the additional sample solution to the decantation chamber.

10. The method according to claim 1, further comprising:
   recording the measured cell density of the sampled cell solution;
   calculating an adjusted amount of the sample of the cell solution that would produce a cell density greater than or equal to the threshold minimum cell density; and
   producing an additional cell analysis plate utilizing said calculated adjusted amount.

11. The method according to claim 1, wherein the cells are uterine cervix cells.

12. A method for performing medical diagnosis of a cell sample from a subject, comprising:
   obtaining a sample of said cells from the subject and placing the cells in a solution in a sample flask;
   taking a sample of said cell solution from the sample flask and placing the sampled solution in a decantation chamber which is arranged above an analysis plate;
   measuring, directly in the decantation chamber, a cell density of the sampled cell solution;
   comparing the measured cell density with a threshold minimum cell density sufficient for said diagnosis, and if the measured cell density is less than the threshold minimum cell density, taking an additional sample of the cell solution from the sample flask and adding the additional sample solution to the decantation chamber, wherein the additional sample provides enough cells to raise the cell density to greater than or equal to the threshold minimum cell density; and
   decanting the cell solution to allow the cells to form a thin layer of cells on the analysis plate, the layer having a cell density sufficient for the medical diagnosis; and
   analyzing the cells on the analysis plate for said medical diagnosis.

13. The method according to claim 12, wherein the medical diagnosis is screening for cervical cancer of the uterus.

* * * * *